United States Patent [19]

Jones

[11] Patent Number: 4,880,985
[45] Date of Patent: Nov. 14, 1989

[54] DETACHED COLLIMATOR APPARATUS FOR RADIATION THERAPY

[76] Inventor: Douglas Jones, 11618 - 20th St. Southeast, Everett, Wash. 98205

[21] Appl. No.: 253,597

[22] Filed: Oct. 5, 1988

[51] Int. Cl.$^4$ .............................................. H01J 29/46
[52] U.S. Cl. .............................. 250/505.1; 250/492.3; 378/147
[58] Field of Search .......................... 250/505.1, 492.3; 378/147, 150

[56] References Cited

U.S. PATENT DOCUMENTS

| | | | |
|---|---|---|---|
| 2,533,701 | 12/1950 | Watt et al. | 250/399 |
| 2,998,526 | 8/1961 | Green et al. | 378/147 |
| 3,944,836 | 3/1976 | Piret et al. | 378/147 |
| 4,122,350 | 10/1978 | Lipthay et al. | 378/37 |
| 4,140,129 | 2/1979 | Heinz et al. | 250/505.1 |
| 4,220,866 | 9/1980 | Taumann et al. | 250/505.1 |
| 4,277,585 | 7/1981 | Covic | 378/7 |
| 4,314,158 | 2/1982 | Lucido | 250/505.1 |
| 4,484,078 | 11/1984 | Tayag et al. | 250/505.1 |
| 4,528,453 | 7/1985 | Heller | 250/505.1 |
| 4,602,377 | 7/1986 | Schiferl et al. | 378/150 |

FOREIGN PATENT DOCUMENTS 31124824 7/1973 Fed. Rep. of Germany .
3124824 1/1981 Fed. Rep. of Germany .
57-161575 10/1982 Japan .
65165571 8/1985 Japan .

OTHER PUBLICATIONS

"Improved Collimation System for Diamond-Anvil High Pressure Cells", by Schiferl et al., Rev. Sci. Instrum., 54(9), Sep. 1983, (pp. 1250-1251).

*Primary Examiner*—Carolyn E. Fields
*Assistant Examiner*—John A. Miller
*Attorney, Agent, or Firm*—Keith S. Bergman

[57] ABSTRACT

A collimator apparatus is disclosed for directing a high energy electron beam from an accelerator through an exit aperture and through a spaced and non-connected collimator tube in juxtaposition with a target area in a patient. The collimator tube is adjustably positioned and positionally maintained by jig structure supported independently of the accelerator structure. A rod type alignment device is releasably positionable in the collimator tube to define alignment of that tube by a novel method using traditional isocentric motions of a patient couch and accelerator gantry. Collimator tubes of varying diameters and exit configurations may be selectively utilized to accurately conform an electron beam to a particular target area and provide uniform irradiation over that target area.

6 Claims, 3 Drawing Sheets

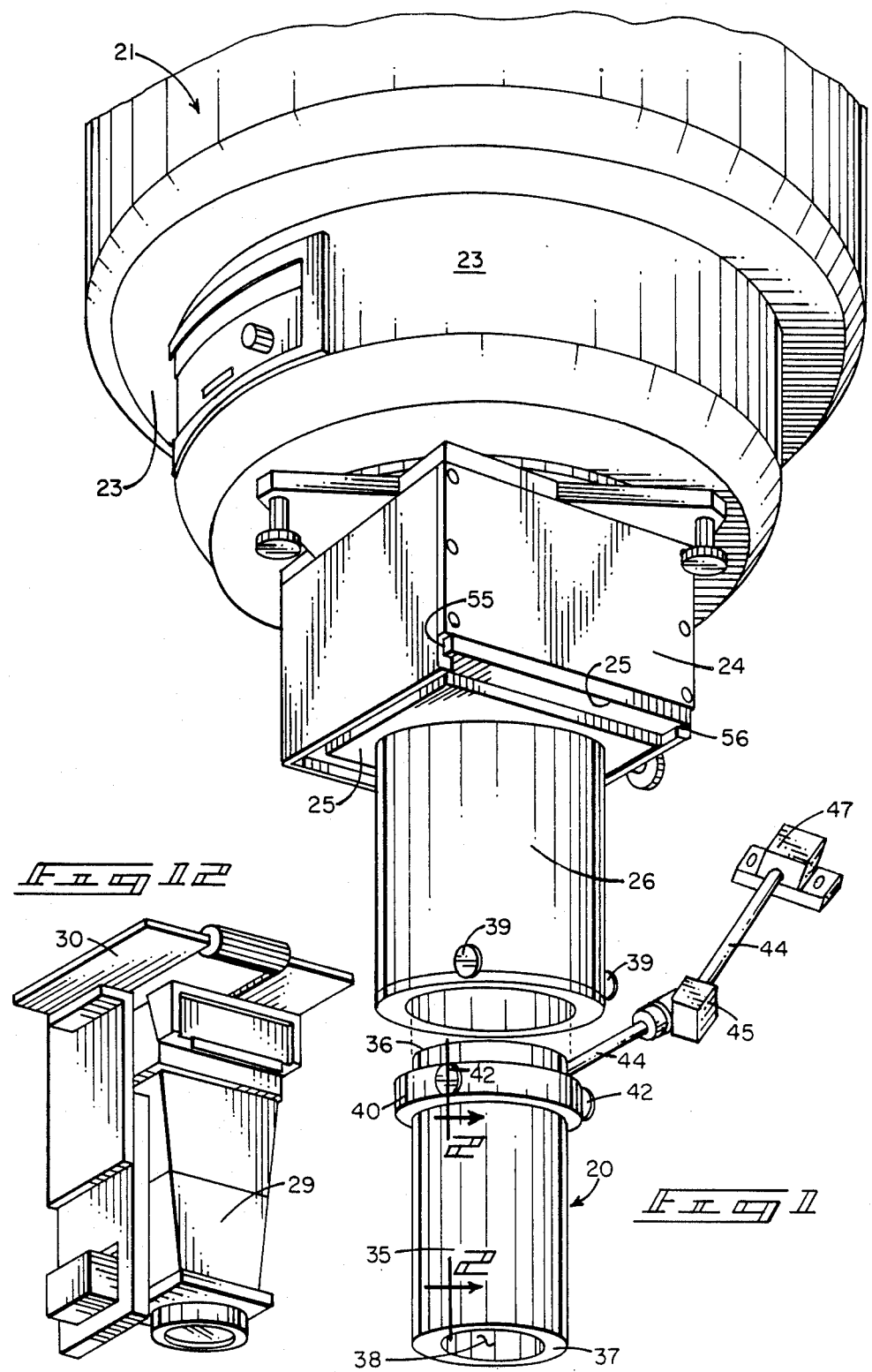

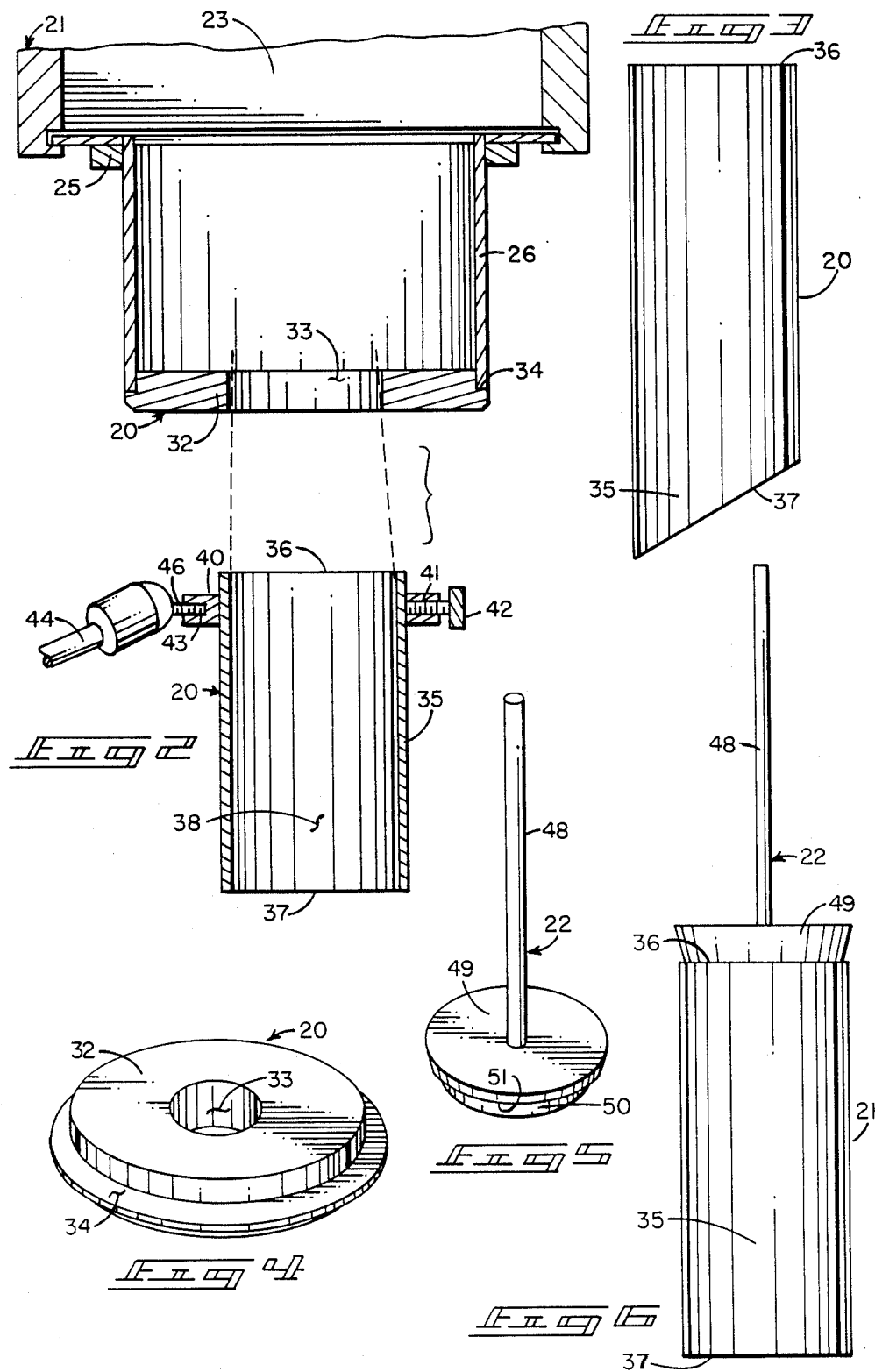

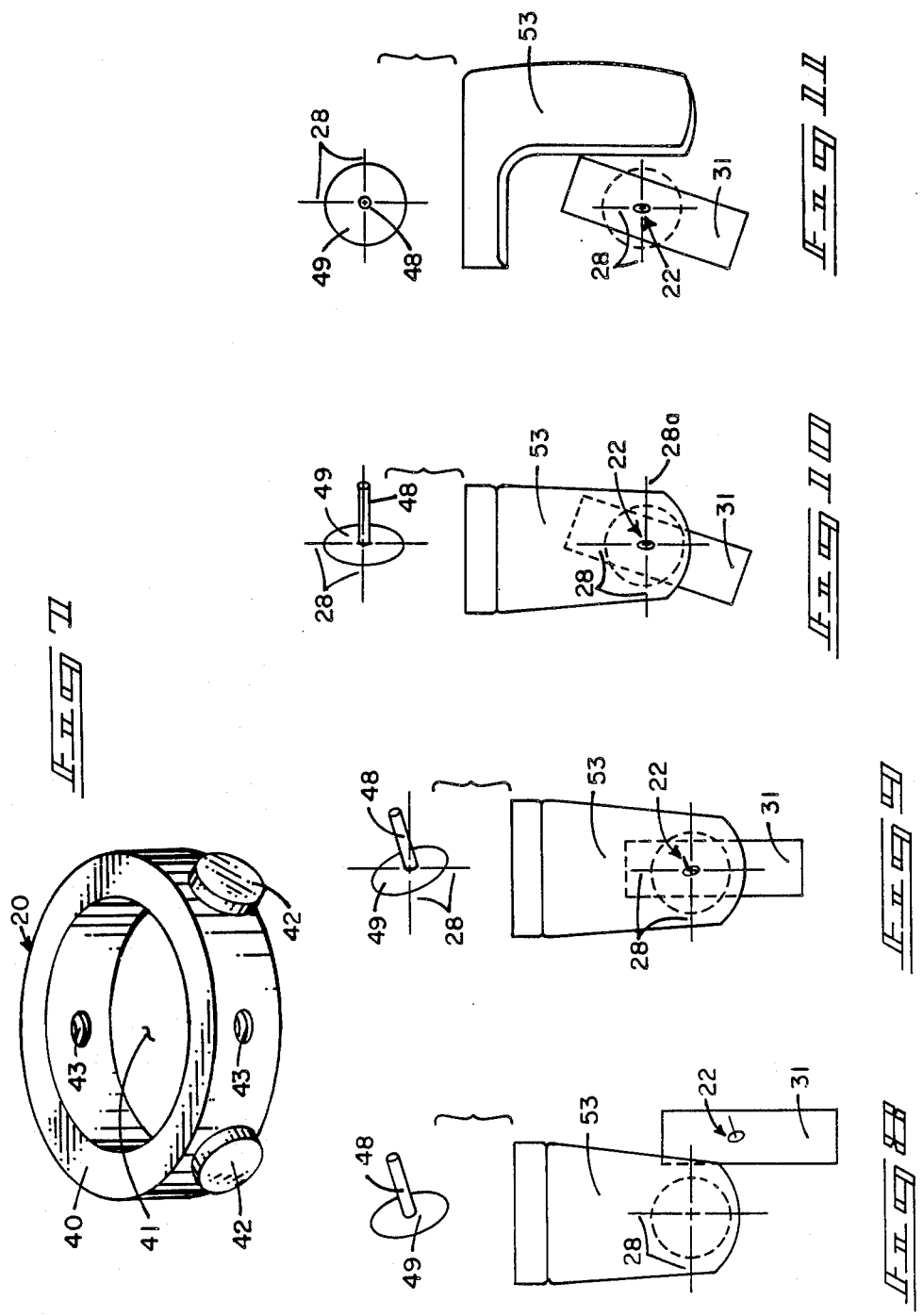

DETACHED COLLIMATOR APPARATUS FOR RADIATION THERAPY

BACKGROUND OF INVENTION

RELATED APPLICATIONS

There are no applications for patent relating hereto heretofore filed in this or any foreign country.

FIELD OF INVENTION

My invention relates to the therapeutic application of electron accelerators and particularly to a collimator securable relative to a patient without connection to an accelerator structure and alignment apparatus for use therewith.

BACKGROUND AND DESCRIPTION OF PRIOR ART

Treatment of various ailments by use of electron radiation is well known in the medical arts. High energy electron beams are commonly directed, either directly or in angulated fashion such as by magnetic field directional apparatus, from their source of origin to a preselected target area by means of associated collimator apparatus. Such collimator apparatus has historically included tubes of pre-selected size and various configurations to accommodate anatomical variations and conditions of patients to be treated and physical parameters of an electron beam to be used.

Apparatus utilized in electron radiation therapy is necessarily relatively expansive and articulation to accurately position and orient a relatively small collimator tube at a precise point of treatment within or on a patient has been rather difficult. This collimator positioning has been further complicated by the historic interconnection of a collimator tube with the output structure of an accelerator, and often also with a patient. The size of an accelerator apparatus and the nature of a beam orienting procedure may cause either physical or emotional damage to a patient during the orientation procedures. Efforts to accurately determine the positioning of collimator assemblies and enable a more precise association of such assemblies with both patient and accelerator have been the source of various activity in the past, but because of the delicacy and nature of the apparatus involved and the sensitivity, both physically and emotionally of patients, prior art devices have not well satisfied the need for either apparatus or methods that have both precise positioning ability and appropriate delicacy of patient association.

My invention overcomes deficiencies of prior art devices by providing collimator apparatus that may be precisely orientated within or without a patient positioned for treatment and is oriented and arranged to delicately associate and dock an expansive electron acceleration apparatus required in this class of medical treatment. The instant invention achieves this function by providing a collimator assembly that is maintained spacedly adjacent but not physically secured to or interconnected with an accelerator. Output of the associated linear accelerator is directed to my collimator through an aperture defined in an aperture plate releasably secured to a collimator cylinder carried by the linear accelerator proximate the output aperture of its radiation beam. My collimator tube is secured to a jig mechanism carried separably from the accelerator, and generally by a patient couch, independent of both the accelerator structure and a patient. The jig device includes plural rods articulately joined to allow universal positioning and positional maintenance of my collimator tube with any type of axial alignment and three-dimensional position.

Pre-selected collimator tubes of various configurations are utilized, but generally of cylindrical shape, of inside diameter varying from two to four inches, and of terminal face configuration varying through included angles from zero to about thirty degrees from the tube axis. Such configurations regulate not only target area size and shape, but also aid in creating a substantially flat or uniform radiation pattern over that field. The collimator tubes are formed of aluminum, in contradistinction to polymeric materials of the prior art, and this allows color coding of various tubes by dying an anodized coating and ready sterilization by autoclaving. The independence of my collimator tube relative to an accelerator structure allows use of traditional camera apparatus both to record treatment areas and apparatus alignment and also allows optical viewing at any time.

I provide an elongate alignment rod carried by an associated flange that is releasably positionable within the accelerator facing of a collimator tube, in coaxial alignment therewith, to serve as a target and alignment device for positioning of the target area in the patient relative to the linear accelerator. Accelerators of the type to be serviced provide optical alignment means directed through their electron beam output apertures to direct the beam to a target area. Such optical alignment means allow precise targeting by alignment of the alignment rod axis with an output beam of an accelerator by a novel alignment process. After positioning of my collimator tube relative to a patient supported on a mobile couch, the alignment rod flange is positioned in my collimator tube with the alignment rod extending toward the accelerator. The couch is then moved relative to the accelerator gantry to position the cross-hair field light at the base of the alignment rod. The couch is then rotated substantially about the alignment rod base until the horizontal cross-hair of the accelerator periscope is axially aligned with the alignment rod. The accelerator gantry is then pivoted until only the end of the alignment rod is seen, with the periscope cross-hair intersection at the axis of the alignment rod. The collimator tube then is axially aligned with the center of a potential electron beam from the accelerator. Such an alignment process was neither allowed nor required with prior art collimators that were interconnected to the accelerator structure.

My invention resides not in any one of these features per se, but rather in the synergistic combination of all of them to gives rise to the structures of my invention and the functions necessarily flowing therefrom, as hereinafter more particularly specified and claimed.

SUMMARY OF INVENTION

A separated collimator assembly, having plural selectable collimator tubes and alignment apertures, is disclosed for a high energy electron linear accelerator. An aperture defining structure is provided for releasable carriage by the existing output beam structure of an accelerator. A collimator tube is securable to a jig mechanism for adjustable positioning relative to a patient and an associated accelerator at a spaced distance from the accelerator. The jig mechanism includes plural rods secured to a flange orthogonally secured to the collimator tube for universal positioning and positional maintenance of that tube. An alignment rod carried by an associated support disk is coaxially mountable within the collimator tube for alignment and orientation of both patient and linear accelerator apparatus in docking relative to the collimator tube, as aided by the existing gantry structure and optical alignment system of the accelerator.

A particular novel alignment method: (1) positions the collimator relative to a patient on a movable couch, (2) positions the couch by locomotion to align the alignment rod base with the accelerator electron beam axis, (3) positions the couch by rotation to align the alignment rod axis with the plane of accelerator gantry rotation, and (4) rotates the gantry to axially align the alignment rod and a potential electron beam.

In creating such a device, it is:

A principal object of my invention to provide a modular collimator apparatus having plural selectable collimator tubes positioned independently of an associated accelerator to direct high energy electron beams to a target area in a human patient for therapy.

A further object of my invention to provide such an apparatus wherein a patient collimator tube is supported, for universal motion and positioning by an articulating jig structure, in spaced adjacency to an associated electron accelerator and also to a patient.

Another object of my invention to provide plural collimator tubes having varying sizes and exit aperture configurations to finely regulate definition of a radiation target area and uniformity of irradiation thereof.

Another object of my invention to provide collimator tubes formed of aluminum to allow sterilization by autoclaving and color coding by dying of an anodized coating thereon.

Another object of my invention to provide such collimating apparatus that allows target viewing or photography by existing accelerator systems at any time except during irradiation.

Yet another object of my invention to provide a novel method of aligning the electron beam of a linear accelerator with a separated, universally positionable collimator tube associated therewith.

Yet another object of my invention to provide such collimator apparatus that is usable with existing commercial linear accelerators without modification or special adaptation of such accelerators.

Still another object of my invention to provide such collimator apparatus that has an alignment rod releasably positionable within a collimator tube to aid alignment with the beam path of a servicing electron accelerator.

A still further object of my invention to provide such apparatus methods for its use that are new and novel, of rugged and durable nature, of simple and economic manufacture, and are otherwise well suited for the functions and purposes for which they are intended.

Other and further objects of my invention will appear from the following specification and accompanying drawings which form a part hereof. In carrying out the objects of my invention, however, it is to be understood that its essential features are susceptible of change in design and structural arrangement with only one practical and preferred embodiment being illustrated in the accompanying drawings, as is required.

BRIEF DESCRIPTION OF DRAWINGS

In the accompanying drawings wherein like numbers of reference refer to similar parts throughout:

FIG. 1 is an isometric view of the output beam structure of a typical electron linear accelerator, showing the aperture structure of my invention in operative position thereon with an associated collimator tube in spaced adjacency.

FIG. 2 is a partial orthographic cross-sectional view of the support and collimator tubes of FIG. 1, taken on the line 2—2 of that Figure in the direction indicated by the arrows.

FIG. 3 is an orthographic view of a collimator tube having different size and exit orifice configuration than that of FIG. 1.

FIG. 4 is an isometric view of the aperture element of my invention.

FIG. 5 is an isometric view of the alignment rod and its support disk.

FIG. 6 is an orthographic view of the alignment structure of FIG. 5 in place for use in a collimator tube.

FIG. 7 is an isometric view of the positioning ring of my invention.

FIGS. 8–11 are diagrammatic illustrations showing the steps of using my invention for alignment of a collimator tube, supported on a patient couch, with an associated accelerator gantry.

FIG. 12 is an illustration of a typical known camera structure for use in photographing a radiation site.

DESCRIPTION OF THE PREFERRED EMBODIMENT

My invention generally provides collimator apparatus 20, associated with alignment member 22 to aid in aligning the collimator apparatus with an output beam of conventional linear accelerator 21.

The output beam structure of a typical present day linear accelerator 21 is illustrated in FIG. 1. High energy electrons are generated within, accelerated by and directed outwardly from the accelerator through an exit port defining an orifice or "window" in accelerator exit port structure 23 which is supported ultimately by a gantry mechanism for adjustable motion. A given geometric cross-sectional opening in the accelerator exit port structure is matched by a similar compatible opening in exit support base 24 for substantially linear passage of a coherent beam of high energy electrons therethrough. Support base 24 is configured to slidably received accelerator collimator tube base plate 25 between complementary channels 55 and 56 defined in spaced relationship in the exit portion of the exit support base. Base plate 25 defines an orifice for passage of an electron beam and structurally carries depending accelerator collimator cylinder 26 which also defines an internal channel for passage of an output electron beam therethrough. Both exit support base 24 and collimator cylinder 26 may be formed in various sizes and with various configurations, dependent upon configuration and radiation requirements of a particular accelerator.

A periscope device is provided inside the output beam structure 21 of the radiotherapy accelerator with a cross-hair 28 accurately aligned to the electron beam axis, as shown diagrammatically in FIGS. 8 through 11 and hereinafter discussed. These cross-hairs are generally so oriented as to define each of the two possible axes that are perpendicular to the axis of gantry rotation, which commonly is the horizontal axis.

Optical camera device 29, as illustrated in FIG. 12, is provided to photograph a treatment site to show its location, nature, and machine alignment therewith. Such camera device is carried on mounting structure 30 which provides a base portion that is releasably carried between tracks 55 and 56 defined in the exit support base so that the accelerator collimator structure may be removed and the camera device inserted. The camera elements are so arranged that the optical center of the camera is substantially coincident with the axis of the accelerator collimator tube and periscope when either are properly associated with, and releasably carried by, the exit support base. The optics of camera 29 are so adjusted and regulated to photograph substantially the same area that will be irradiated by an output beam of a particular linear accelerator.

Positioning of linear accelerators of the relevant class is generally accomplished by mounting output structure 23 in a gantry mechanism that is pivotal about at least one axis and possibly movable in other directions. Universally, the gantry will pivot about a horizontal axis for motion in a vertical plane.

Commonly a patient to be irradiated will be supported on couch or table 31 which is movable for locomotion over an underlying supporting surface, such as a floor, and has means for adjustable vertical positioning of a patient relative to that underlying supporting surface. Such couches are well known in tee radiation therapy arts and their use is almost universal with the instant gantry type of accelerator. With such couch and gantry mechanism, a patient is commonly positioned for radiation by adjustably positioning both the patient couch and the gantry structure carrying the output orifice of a linear accelerator. Since this positioning involves motion of two independently movable structures in three-dimensional space, it has been a reasonably complex operation and it becomes even more complex if the ultimate patient collimator tube 35 is physically separated from the linear accelerator structure. My invention provides such separation and yet provides a simple and easy means of positioning the various elements relative to each other in proper irradiation alignment.

The couch and accelerator structure heretofore described is known in the prior art and though necessary for use with my invention, it does not comprise my invention per se.

My invention provides patient collimator apparatus 20 having an orifice defining element carried by the accelerator collimator tube and a separated patient collimator tube that is positionally aligned with an accelerator output structure by alignment member 22.

My collimator apparatus provides aperture disk 32 releasably carried by accelerator collimator tube 26. This aperture disk is an annular structure, as illustrated in FIG. 1, with a configuration similar to that of the accelerator collimator tube 26, normally circularly cylindrical. The aperture disk defines medial orifice 33 for passage of at least a portion of an already somewhat collimated radiation beam. The circular peripheral surface of the disk, at one edge, defines annular channel 34 configured to allow the accelerator facing or inward portion of the aperture disk to be matingly received within the bore of accelerator collimator cylinder 26, as illustrated. That accelerator collimator cylinder is commonly provided with plural fastening screws 39 threadedly engaged therethrough to releasably fasten auxiliary structures, such as aperture disk 32, in that tube by reason of frictional engagement therewith. The size of orifice 33 normally will not be greater than, and is limited by, the size of the aperture of patient collimator tube 35 to prevent dispersement of a radiation beam outside that tube.

Patient collimator tube 35 comprises a peripherally defined cylinder with perpendicular inner end 36, variously angled output end 37, and collimator channel 38 communicating therebetween. The collimator channel may be of varying shape and size, but most commonly it is of a circular cross-sectional configuration. Output end 37 of the tube may be of various configurations, but commonly it will define the intersection of a plane with the cylinder, with the angle of the defining plane varying generally up to an included angle of approximately 60-90 degrees with the cylindrical axis.

The geometric configuration of the patient collimator tube will not only define the target area to be irradiated, but also may effect the intensity of radiation over that target area, depending somewhat upon the nature of the beam that is collimated by the device. Various analyses of the effects of geometric parameters in linear accelerator collimators have heretofore been published and in general, those principles relate to my invention. Both the length and diameter of the tube may be adjusted to regulate the paths of individual electrons and thus ultimately regulate the uniformity of an irradiated field. The shape of the exit orifice of the collimator also will effect the pattern of radiation, its intensity and distribution over the field at the point it is applied to a patient. Commonly I prefer circularly cylindrical collimator tubes having an axial length of about 150 to 200 millimeters and an internal diameter varying from about 50 to 100 millimeters when used with electron accelerators common in modern radiation therapy. I have found aluminum collimators of such configuration to have flatness ratios varying approximately from 0.8 to 1.1 with nominal particle energy values varying from 6 to 18 MeV.

My collimator structures may be formed of most any rigid, reasonably radiation opaque materials. Commonly in the prior art, collimator tubes for similar purposes have been formed of polymeric plastic materials. I prefer, however, to form both my aperture element and patient collimator tube from aluminum having an oxidized or so-called "anodized" coating on its surface. Both this material and its coating are very stable both chemically and physically and the nature of the anodized coating is such that it has an open enough pore structure to allow dying with various coloring dyes, according to processes heretofore well known. Aluminum has added advantages over plastic materials in that it may be permanently colored to provide a color coding for various sizes and configurations of elements and the aluminum elements may also be readily sterilized thermally in an autoclave, whereas neither of these functions may be so readily accomplished, if at all, with plastic materials.

Annular attachment ring 40 provides means for attachment of a positioning jig to positionally associate and maintain a patient collimator tube relative to a patient. The attachment ring is an annular structure defining internal channel 41 appropriately sized to fit immediately outwardly adjacent the outer surface of patient collimator tube 35 and has sufficient thickness to support that tube for stable positional maintenance. The positioning ring defines plural threaded holes extending therethrough to receive screws 42 to releasably maintain the ring upon a patient collimator tube being serviced. The external circular periphery of the fastening ring defines at least one inwardly extending threaded hole 43 to allow fastening of a positioning jig arm by threaded engagement therein.

The fastening jig provides at least two arms 44 interconnected for articulating motion by joint 45. One end portion of the jig structure carries threaded stud 46 to threadedly engage within hole 43 defined in positioning ring 40. The second end portion of the positioning jig is releasably carried in clamp structure 47 commonly, but not necessarily, structurally carried by a patient couch. This type of fastening jig structure is known in both the medical and laboratory arts and is not an element, per se of my invention, though its use is necessary in some form or other for operation of my invention.

Alignment member 22 provides straight elongate alignment rod 48 structurally carried by base disk 49. The base disk is of a shape similar to that of the channel of the patient collimator tube but somewhat larger. In its peripheral circular edge, the disk defines annular channel 50 that has a diameter substantially the same as that of the patient collimator tube channel so that this end portion of the base may be received in a slidable fit in the collimator tube channel with sufficient friction to positionally maintain the device during use. The inward surface 51 of the channel 50 should be accurately defined in a plane parallel to the base disk surface and perpendicular to its axis. Alignment rod 48 must be accurately aligned with the base disk so that the rod axis is coincident with that of the base disk and the axis of the channel defined by the patient collimator tube when the member is carried by that tube. The alignment rod is preferably, though not necessarily, of circular cylindrical shape and it should have a diameter of not more than about 6 millimeters and a length of approximately 20 centimeters to accomplish the alignment accuracy normally required and expected in linear accelerators of the type which it is to service. This alignment structure may be formed of any appropriate rigid materials such as one of the harder, more dense polymeric or resinous plastics, but I prefer aluminum for both the base disk and alignment rod.

Having thusly described my invention, its operation may be understood, particularly with reference to FIGS. 8 through 11 of the drawings.

A collimator and alignment apparatus are created according to the foregoing specification with a patient collimator tube of appropriate size and exit orifice configuration to irradiate a particular subject target in desired fashion. Aperture disk 32 is then positioned in the outward end portion of accelerator collimator tube 25 and there releasably fastened by manipulation of set screws 52.

Positioning ring 40, of appropriate size for the chosen patient collimator tube, is then threadedly engaged with stud 46 of the positioning jig so that the positioning ring is supported thereby. The positioning jig commonly will be supported on a couch which is to support a patient during treatment. The selected patient collimator is then inserted within channel 41 defined by positioning ring 40 and releasably fastened within that ring by tightening screws 42 against the external surface of the collimator tube.

A patient is placed on a patient couch, either before or after positioning of the collimator tube on the positioning jig structure, with the target area to be irradiated positioned for appropriate access by beamed radiation, normally from above. The positioning jig is then adjusted to position the exit orifice of the patient collimator tube on, or immediately spacedly adjacent, the target area to be irradiated, with its axis defining the axis of a desired impinging radiation beam, and the jig is releasably fastened in this position. The radiation target area may be on the body surface, within body cavities, in incisions, or generally any place irradiation may be carried out. If desired or necessary, the patient collimator tube may be further secondarily supported in its positioning relative to a patient by weighted bags, adhesive tape or other similar means heretofore known in the radiation therapy arts.

To align the patient collimator tube with the radiation beam of an accelerator, the alignment structure is positioned in the inner or input end 36 of patient collimator tube 35 with alignment rod 48 projecting inwardly toward the accelerator support collimator tube 26. The alignment rod base 49 should be accurately positioned in the patient collimator tube to assure that the alignment rod is axially aligned with the axis of that tube, but this condition automatically results from the structure disclosed if it be properly formed and assembled as indicated.

Patient couch 31 is then moved to the area of gantry structure 53 which commonly is carried in a room at a spaced distance above the floor for pivotal motion about a horizontal axis. This positioning of elements is illustrated semi-diagrammatically in FIG. 8 where the alignment rod is seen on the patient couch 31 as it would appear in a patient collimator and also enlarged in a separate diagram at the top of the illustration as it would be seen by an operator viewing it. The superimposed crossed lines illustrate crosshairs as would be seen in an optical periscope of the accelerator.

The patient couch is then moved under gantry structure 53 until the center of the base of alignment rod 48 is coincident with the intersection of cross-hairs 54, as shown in FIG. 9 of the drawings. Patient couches for use with modern day radiation therapy accelerators are provided with means for locomotion over an underlying supporting surface; such as a floor, some such means require manual manipulation to accomplish locomotion and others are mechanically activated and controlled. My system is operative with either type of patient couch.

The patient couch is then rotated, substantially about a vertical line passing through the center of the base of the alignment rod, until cross-hair 54a, that is in the plane of rotation of the gantry, aligns with the axis of the positioning rod while the intersection of the two cross-hairs remains at the center of the base of that rod, all as illustrated in the diagrams of FIG. 10. This motion again is accomplished manually or mechanically, depending upon the nature of a particular patient couch. After such positioning, the patient couch is raised or lowered by its associated mechanism as may be required to position the patient relative to the gantry structure in such fashion that when the gantry be rotated into final alignment, the accelerator collimator tube will be at appropriate spaced distance from the patient collimator. Normally, this distance will be at least the 20 centimeter length of the alignment rod, but may be somewhat greater if desired. The patient collimator will then be aligned in the plane of rotation of the accelerator gantry structure and at an appropriate distance from the output end of the accelerator support collimator.

The accelerator gantry is then rotated in appropriate direction to minimize the shadow cast by the alignment rod and until the center of the top of the rod substantially comes into coincidence with the centers of the bottom of the rod and the intersection cross-hairs 28 of the optical periscope. When this occurs, the geometrical axis of the patient collimator tube will be lineally coincident with the axis of the accelerator collimator tube, again as illustrated in FIG. 10 of the drawings. The patient collimator is then properly aligned for radiation treatment, but yet is at a spaced distance from the accelerator collimator tube output orifice and is totally unconnected to and independent of the accelerator structure.

Radiation may now be carried out in its normal fashion and a radiation beam will pass from the accelerator through the patient collimator tube for dispersement through the output orifice of that tube upon a target area to be irradiated.

It should be noted that at any stage of the alignment procedure the accelerator support base and collimator tube may be removed and replaced with camera device 29 to record the particular relationship of a target area of a patient relative to a potential radiation beam for record and evidential purposes. It should further be noted that with use of my invention all of the ordinary and customary alignment devices of the common present day linear accelerators may be used, such as distance indicators, alignment lasers and the like. In general, my alignment device merely provides an additional and ancillary aid for precise alignment of separated patient collimators that does not interfere with existing alignment structures and devices.

It should further be noted that my patient collimator is totally separated from the linear accelerator structure by an air gap. Normally this gap will be at least 10 centimeters.

The foregoing description of my invention is necessarily of a detailed nature so that a specific embodiment of it might be set forth as required, but it is to be understood that various modifications of detail, rearrangement and multiplication of parts might be resorted to without departing from its spirit, essence or scope.

Having thusly described my invention, what I desire to protect by Letters Patent, and what I claim is:

1. A separated collimator and alignment apparatus for use with linear electron accelerators having a beam output structure supported by a gantry and an associated patient couch movable in three-dimensional space relative to said gantry, comprising, in combination:
   an aperture structure defining an orifice for passage of an electron beam therethrough, said aperture structure being releasably carried by an accelerator collimator tube and said orifice being similarly configured to and not larger than an aperture defined in a patient collimator tube;
   the patient collimator tube defining a first medial channel for passage of a coherent electron beam and defining a planar input end facing the aperture structure and an exit end distal therefrom;
   an annular positioning ring defining a second medial channel to fit about the periphery of the patient collimator tube, said positioning ring defining first means for attachment to a positioning jig mechanism and second means for releasable and adjustable positional maintenance upon the patient collimator tube;
   the positioning jig mechanism having at least two rigid rods joined for articulating motion with said first means at a first end to fastenably interconnect with the positioning ring and said second means at a second end for support on a structure external of an electron accelerator to be serviced; and
   an elongate alignment rod carried by a base support disk releasably positionable in a first inner accelerator facing end of the patient collimator tube to aid axial alignment of the alignment rod with the patient collimator tube.

2. The apparatus of claim 1 wherein the patient collimator tube:
   is formed of aluminium with an anodized coating selectively dyed to provide color identification, and
   the collimator tube is configured as a circulator cylinder with a diameter between 50 and 110 millimeter and a length varying between 150 and 200 millimeter.

3. The apparatus of claim 1 wherein the patient collimator tube is further characterized by the exit orifice defined in the exit end being a planar surface angled at an included acute angle with the axis of the patient collimator tube of between 60 and 90 degrees.

4. The apparatus of claim 1 wherein the alignment rod is formed of stainless steel with a length of approximately 200 millimeters and a diameter of approximately 6 millimeters.

5. A method of aligning a separated patient collimator tube with an output beam of an associated linear accelerator having the accelerator collimator tube carried by a gantry structure movable in a room in a vertical plane about a horizontal axis and having an associated patient couch with means for locomotion over the floor of the room adjacent the gantry structure and means for vertical positioning of its supportative surface, comprising the steps of:
   fastening a positioning jig for support on the patient couch;
   positioning a patient for support on the patient couch with an irradiation target area accessible from an upward direction;
   fastening a positioning ring to a first end of the positioning jig;
   fastening the patient collimator tube in the positioning ring;
   positioning the patient collimator tube with an exit orifice adjacent the patient target area to be irradiated and with its axis defining the axis of a radiation beam to be used;
   placing of an alignment apparatus in an input end of the patient collimator tube with an alignment rod extending away from the patient collimator tube;
   moving the patient couch under an output beam structure carried by the gantry of the associated accelerator so that the axis of the output beam, as determined by an optical periscope provided by the linear accelerator, passes through the intersection of the axis of the alignment rod with its base;
   rotating the patient couch to a position wherein the axis of the alignment rod aligns with the vertical plane of rotation of the output beam of the associated accelerator, as evidenced by alignment of a periscope cross-hair with the axis of the alignment rod;
   rotating the gantry structure until the axis of the alignment rod is aligned with the axis of the output beam of the associated accelerator, as evidenced by the centering of the accelerator periscope's cross-hairs simultaneously upon the intersections of the alignment rod axis with both of its ends.

6. A method for aligning a patient collimator tube, supported independently of an associated linear accelerator, with an output beam of the associated linear accelerator having an accelerator collimator tube, defining an output orifice, carried by a gantry for motion at a spaced distance above a floor in a vertical plane about a horizontal axis and having an associated patient couch structure with means for locomotion over the floor adjacent the gantry and means for adjustable vertical positioning of the couch supportive surface, comprising the steps of:

(1) supporting a patient on the patient couch with a radiation target area accessible from above;

(2) positioning and positionally maintaining an elongate patient collimator tube, defining a collimator channel, relative to the patient in orientation to direct a collimated beam of radiation upon a desired target area;

(3) releasably positioning a support disk having an elongate alignment rod in the end of the patient collimator tube distal from the patient with the alignment rod axially coincident with the patient collimator tube;

(4) moving the patient couch over its supporting floor to a position relative the gantry whereat the axis of the output beam from the linear accelerator passes through the center of the base of the alignment rod and that rod, if angled to the accelerator beam axis, is in the plane of rotation of the gantry, as evidenced by the optical alignment means provided by the accelerator;

(5) rotating the gantry until the axis of the alignment rod is substantially coincident with the axis of a potential output beam of the linear accelerator.

* * * * *